US005962010A

United States Patent [19]

Greff et al.

[11] Patent Number: 5,962,010

[45] Date of Patent: Oct. 5, 1999

[54] METHODS AND COMPOSITIONS FOR TREATING DERMATOSES

[75] Inventors: Richard J. Greff, St. Pete Beach, Fla.; Connie C. Lee, Littleton, Colo.

[73] Assignee: MedLogic Global Corporation, Colorado Springs, Colo.

[21] Appl. No.: 08/963,265

[22] Filed: Nov. 3, 1997

[51] Int. Cl.$^6$ .................................................. A61L 25/00

[52] U.S. Cl. .................................................. 424/443

[58] Field of Search .................................................. 424/443

[56] References Cited

U.S. PATENT DOCUMENTS

| | | | |
|---|---|---|---|
| 3,527,224 | 9/1970 | Rabinowitz . | |
| 3,591,676 | 7/1971 | Hawkins et al. . | |
| 3,654,239 | 4/1972 | McIntire et al. . | |
| 3,667,472 | 6/1972 | Halpern . | |
| 3,995,641 | 12/1976 | Kronenthal et al. . | |
| 4,035,334 | 7/1977 | Davydov et al. . | |
| 4,038,345 | 7/1977 | O'Sullivan et al. . | |
| 4,650,826 | 3/1987 | Waniczek et al. . | |
| 5,286,491 | 2/1994 | Amkraut et al. | 424/443 |
| 5,480,935 | 1/1996 | Greff et al. | 524/776 |
| 5,684,042 | 11/1997 | Greff et al. | 514/527 |
| 5,762,955 | 6/1998 | Smith | 424/443 |

OTHER PUBLICATIONS

Blum, et al., In Vitro Determination of the Antimicrobial Properties of Two Cyanoacrylate Preparations, J. Dent Res., 54:(3):500–503 (1975).

*Primary Examiner*—Peter F. Kulkosky
*Attorney, Agent, or Firm*—Burns, Doane, Swecker & Mathis, LLP

[57] ABSTRACT

A cyanoacrylate ester composition comprising a corticosteroid is applied to skin lesions associated with dermatosis or dermatitis to protect and/or treat such lesions.

31 Claims, No Drawings

METHODS AND COMPOSITIONS FOR TREATING DERMATOSES

BACKGROUND OF THE INVENTION

Field of the Invention

This invention is directed to methods and compositions for treating active dermatoses (e.g., dermatitis, psoriasis and eczema).

Specifically, in one aspect, this invention is directed to methods for forming in situ a coherent polymeric film over the active dermatosis by topical application of a polymerizable cyanoacrylate ester composition to the affected skin areas and subsequent polymerization of the composition. The coherent polymeric film acts as an occlusion layer over the affected skin areas. Preferably, the polymerizable cyanoacrylate ester composition comprises a corticosteroid which is released from the polymeric film in therapeutically effective amount.

In another aspect, this invention is directed to cyanoacrylate ester compositions comprising polymerizable cyanoacrylate esters and a therapeutically effective amounts of at least one corticosteroid. Optionally, these compositions further comprise an antimicrobial agent to inhibit microbial infections under the polymeric film.

References

The following publications, patents and patent applications are cited in this application as superscript numbers:

1 Askill, et al., U.S. patent application Ser. No. 08/912,678, for *Methods for Draping Surgical Incision Sites*, filed Aug. 18, 1997

2 Remington's Pharmaceutical Sciences, 17th Edition, 1985

3 Hawkins, et al., *Surgical Adhesive Compositions*, U.S. Pat. No. 3,591,676, issued Jul. 6, 1971

4 Halpern, et al., *Adhesive for Living Tissue*, U.S. Pat. No. 3,667,472, issued Jun. 6, 1972

5 Rabinowitz, et al., *Method of Surgically Bonding Tissue Together*, U.S. Pat. No. 3,527,224, issued Sep. 8, 1970

6 Kronenthal, et al., *Surgical Adhesives*, U.S. Pat. No. 3,995,641, issued Dec. 7, 1976

7 Davydov, et al., *Medical Adhesive*, U.S. Pat. No. 4,035,334, issued Jul. 12, 1977

8 Waniczek, et al., *Stabilized Cyanoacrylate Adhesives Containing Bis-Trialkylsilyl Esters of Sulfuric Acid*, U.S. Pat. No. 4,650,826, issued Mar. 17, 1987

9 McIntire, et al., U.S. Pat. No. 3,654,239, for *Process for the Preparation of Poly(α-Cyanoacrylates)*, issued Apr. 4, 1972

10 O'Sullivan, et al., U.S. Pat. No. 4,038,345, for *High Viscosity Cyanoacrylate Adhesive Compositions, and Process for Their Preparation*, issued Jul. 26, 1977

11 Greff, et al., U.S. Pat. No. 5,684,042 for *Cyanoacrylate Compositions Comprising an Antimicrobial Agent* to issue Nov. 4, 1997

12 Greff et al., U.S. Pat. No. 5,480,935, for *Cyanoacrylate Adhesive Compositions* issued on Jan. 2, 1996

13 Blum, et al., In vitro *Determination of the Antimicrobial Properties of Two Cyanoacrylate Preparations*, J. Dent. Res., 54(3):500–503 (1975)

All of the above publications, patent applications and patents are herein incorporated by reference in their entirety to the same extent as if each individual publication, patent application or patent was specifically and individually indicated to be incorporated by reference in its entirety.

State of the Art

Treatment regimens for many mammalian skin diseases such as dermatosis include the topical application of a corticosteroid onto the diseased skin. The corticosteroid is typically formulated as an ointment, cream, lotion, solution, etc., and topical application to the skin is conducted once or more per day until the disease condition abates.

Some dermatoses are characterized by a greatly accelerated rate of epidermal turnover. Normally, skin regeneration is a controlled process where keratinocytes of the epidermal layer regenerate, differentiate and are pushed to the skin surface. There, the keratinocytes cornify, die and are shed. The natural regeneration process generally takes about 28 to 30 days.

In contrast to natural skin regeneration, psoriasis is a chronic disease characterized by epidermal hyperplasia and a greatly accelerated rate of epidermal turnover (hyperproliferation of keratinocytes). The lesions are characteristically red, slightly raised and scaly and can be quite unsightly. The lesions may be localized or generalized and may cause discomfort such as burning and itching.

Topical application of corticosteroids to skin areas undergoing active dermatosis leads to reduced skin inflammation (reduced reddening of the skin) as well as reduced skin itching. By reducing the inflammatory process, corticosteroids can permit healing to occur.

Nevertheless, several problems arise in such treatment regimens. First, direct physical contact of clothing with inflamed irritated skin can cause painful abrasions. Second, after application of the corticosteroid composition, any contact of the treated skin with clothing, water (washing), etc. results in removal of at least a portion of the topically applied corticosteroid thereby lessening the therapeutic effect. Third, in certain skin disease conditions such as psoriasis, the preferred treatment regimen includes occlusion of the skin for prolonged periods of time. Occlusion, however, can lead to unsightly bandages/wraps which may interfere with normal activities particularly where the disease condition is on the arms or legs. Moreover, bathing and other water activities become problematic, at best, when bandages/wraps are placed on the patient. In the case of other dermatoses where bandages are not required, the topical ointments or creams can wash or rub off onto and stain clothing, or in the case of overnight use, bedding.

This invention is directed, in part, to the discovery that in situ formation of a cyanoacrylate polymeric film over the diseased skin overcomes many of the prior art problems recited above. Preferably, the cyanoacrylate composition further comprises a corticosteroid which additionally provides incremental advantages heretofore not achieved by conventional occlusion wraps. For example, the cyanoacrylate polymer is waterproof and forms an occlusion over the diseased skin which permits the patient to bath, wash, swim, etc. without concern that such activities would interfere with the occlusion wrap. Still another advantage is the formation of an appropriately configured wrap without the need to modify the dimensions provided with commercial wraps. Still further, the methods and compositions of this invention result in wraps which mold directly to the multiple contours of the intended occlusion sites. In any event, the corticosteroid is released from the film over time to deliver a therapeutically effective amount of this drug to the skin.

SUMMARY OF THE INVENTION

This invention is drawn to methods and compositions for treating dermatosis and/or protecting the skin lesions commonly associated with such disease conditions by the application of polymerizable cyanoacrylate ester compositions to the surface of such lesions. This invention is based, in part, on the discovery that the in situ formation of a coherent polymeric cyanoacrylate film over such skin lesions provides for an occlusive layer which facilitates healing of the lesions. Moreover, incorporation of a therapeutically effective amount of a corticosteroid into the polymerizable cyanoacrylate ester composition results in a polymeric film which releases the corticosteroid into the lesion and surrounding skin areas to facilitate healing.

Accordingly, in one of its method aspects, this invention is directed to a method for treating dermatosis on mammalian skin surface(s) which method comprises:

(a) applying to the topical surface of the dermatosis a polymerizable cyanoacrylate ester composition;

(b) polymerizing the cyanoacrylate ester composition in situ on said surface so as to form a coherent polymeric film over the dermatosis.

In a preferred embodiment, the cyanoacrylate ester composition further comprises a corticosteroid and/or an antimicrobial agent. The corticosteroid in the polymerizable cyanoacrylate ester composition is incorporated into the resulting polymeric film formed in situ on the mammalian skin and subsequent release of this corticosteroid from the film serves to medicate the dermatosis and decreases discomfort such as itching, while facilitating healing of the skin. The antimicrobial agent serves to inhibit microbial infection of the skin during the healing process.

Preferably, any lesions associated with the dermatosis treated by the methods of this invention do not penetrate the dermal layer. While lesions are characteristic of psoriasis, dermatitis, eczema and the like, such lesions do not typically extend beyond the dermal layer and, accordingly, any incorporation of the polymerized cyanoacrylate ester into these lesions will be temporary. That is to say that such incorporation will terminate when that portion of the skin is shed as part of the natural shedding process.

Since the polymeric cyanoacrylate film is retained on the skin for from 1–4 days after formation and does not easily rub off, the dermatosis is treated more effectively than with the current topical steroid formulations. Without a bandage or covering, these formulations can rub off before the steroid is absorbed by the skin, e.g, onto clothing, thus decreasing the exposure of the corticosteroid to the skin.

Accordingly, in one of its composition aspects, this invention is directed to a cyanoacrylate ester composition which comprises:

(a) a polymerizable cyanoacrylate ester; and (b) a therapeutically effective amount of a corticosteroid.

Preferably, the polymerizable cyanoacrylate ester is a polymerizable monomer or reactive oligomer of a cyanoacrylate ester which, in monomeric form, is represented by formula I:

I

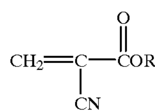

wherein R is selected from the group consisting of:

alkyl of 1 to 10 carbon atoms, alkenyl of 2 to 10 carbon atoms, cycloalkyl groups of from 5 to 8 carbon atoms, phenyl, 2-ethoxyethyl, 3-methoxybutyl, and a substituent of the formula:

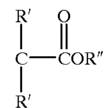

wherein each R' is independently selected from the group consisting of:

hydrogen and methyl, and

R" is selected from the group consisting of:

alkyl of from 1 to 6 carbon atoms, alkenyl of from 2 to 6 carbon atoms, alkynyl of from 2 to 6 carbon atoms, cycloalkyl of from 3 to 8 carbon atoms, aralkyl selected from the group consisting of benzyl, methylbenzyl and phenylethyl, phenyl, and phenyl substituted with 1 to 3 substituents selected from the group consisting of hydroxy, chloro, bromo, nitro, alkyl of 1 to 4 carbon atoms, and alkoxy of from 1 to 4 carbon atoms.

More preferably, in the cyanoacrylate esters of formula 1, R is alkyl of from 2 to 10 carbon atoms and still more preferably alkyl of from 4 to 8 carbon atoms. Even more preferably, R is butyl, pentyl or octyl and most preferably, R is n-butyl.

The corticosteroid (e.g., glucocorticosteroid) is selected to provide a topical anti-inflammatory effect to mammalian skin and to be compatible with the polymerizable cyanoacrylate ester composition, e.g., it does not inhibit polymerization or cause premature polymerization of the composition but rather permits the composition to form a coherent, durable, flexible film on the skin. The corticosteroid is preferably selected from the group consisting of cortisone, desoximetasone, hydrocortisone, betamethasone, fluorinated derivatives, and the like. Preferably, the corticosteroid is employed in the polymerizable cyanoacrylate ester composition at a concentration of from about 0.1 to about 25 weight percent based on the total weight of the composition and preferably a concentration of from about 0.1 to about 10 weight percent based on the total weight of the composition.

Optionally, this composition also comprises an effective amount of an antimicrobial agent to inhibit microbial infection of the lesion under the cyanoacrylate polymeric film. The antimicrobial agent is also selected so that it is compatible with the polymerizable cyanoacrylate ester composition.

Another aspect of this invention is a kit of parts which comprises a polymerizable cyanoacrylate stored in a first container and a corticosteroid stored in a second container. The kit may further comprise an applicator means on the first or second container. The kit may optionally comprise PVP-iodine in a separate container.

DETAILED DESCRIPTION OF THE PREFERRED EMBODIMENTS

This invention relates to methods and compositions for treating and/or protecting dermatotic skin lesions in mammals. However, prior to discussing this invention in further detail, the following terms will first be defined:

The term "cyanoacrylate ester compositions" or "cyanoacrylate compositions" refers to polymerizable formulations comprising polymerizable cyanoacrylate ester monomers and/or oligomers which, in their monomeric form, are preferably compounds represented by formula I as described above.

More preferably, in formula 1, R is an alkyl group of from 2 to 10 carbon atoms including, by way of example, ethyl, n-propyl, iso-propyl, n-butyl, iso-butyl, sec-butyl, n-pentyl, iso-pentyl, n-hexyl, iso-hexyl, 2-ethylhexyl, n-heptyl, n-octyl, nonyl, and decyl. More preferably, R is butyl, pentyl or octyl and most preferably, R is n-butyl. Mixtures of such compounds can also be employed.

Polymerizable cyanoacrylate esters are known in the art and are described in, for example, U.S. Pat. Nos. 3,527,224; 3,591,676; 3,667,472; 3,995,641; 4,035,334; and 4,650,826[3-8] the disclosures of each are incorporated herein by reference in their entirety.

A particularly preferred cyanoacrylate ester for use in the invention is n-butyl-2-cyanoacrylate.

The polymerizable cyanoacrylate ester compositions described herein rapidly polymerize in the presence of water vapor or tissue protein, and the n-butyl-cyanoacrylate bonds human skin tissue without causing histotoxicity or cytotoxicity.

Such polymerizable cyanoacrylate esters are sometimes referred to herein as prepolymers and compositions comprising such esters are sometimes referred to herein as prepolymer compositions.

The term "dermatosis" refers to any topical skin condition amenable to treatment with corticosteroids to reduce the symptoms of the skin condition. Examples of different dermatoses include skin diseases such as psoriasis, dermatitis, eczema, and the like as well as skin irritations arising from contact with alkylcatechols such as found in poison oak, poison ivy, etc. "Dermatotic skin" refers to skin undergoing active dermatosis.

With regard to the above, psoriasis is a chronic disease characterized by epidermal hyperplasia and a greatly accelerated rate of epidermal turnover (hyperproliferation of keratinocytes). The lesions are characteristically red, slightly raised and scaly. Although psoriasis is usually a minor disorder, generalized forms and systemic manifestations also occur. The lesions of psoriasis are discrete or confluent erythematous plaques and papules covered with white or silvery scales, and are characteristically found on the extensor surfaces such as the elbows and knees, and on the back and scalp. The lesions may be localized or generalized and may cause discomfort such as burning and itching.

Dermatitis relates more specifically to inflammation of the skin. An example of dermatitis is eczema, also known a atopic dermatitis. Eczema is an inflammatory skin disease characterized by lesions varying greatly in character, with vesiculation, infiltration, watery discharge and the development of scales and crusts. The disease is also characterized by local itching and burning.

Other examples of dermatosis or dermatitis which may be treated with the methods of this invention are contact dermatitis, eczematous dermatitis, seborrhoeic dermatitis and Lichen planus.

The term "biocompatible plasticizer" refers to any material which is soluble or dispersible in the cyanoacrylate ester composition, which increases the flexibility of the resulting polymer film coating on the skin surface, and which, in the amounts employed, is compatible with the skin as measured by the lack of moderate to severe skin irritation. Suitable plasticizers are well known in the art and include those disclosed in U.S. Pat. Nos. 2,784,127 and 4,444,933 the disclosures of both of which are incorporated herein by reference in their entirety. Specific plasticizers include, by way of example only, acetyl tri-n-butyl citrate (~20 weight percent or less), acetyl trihexyl citrate (~20 weight percent or less), butyl benzyl phthalate, dibutyl phthalate, dioctylphthalate, n-butyryl tri-n-hexyl citrate, diethylene glycol dibenzoate (~20 weight percent or less) and the like. The particular biocompatible plasticizer employed is not critical and preferred plasticizers include dioctylphthalate, and $C_2$–$C_4$-acyl tri-n-alkyl ($C_1$–$C_6$) citrates.

The term "polymerization inhibitor" refers to any material which is soluble or dispersible in the cyanoacrylate ester composition and which, in the amounts employed, inhibits the premature polymerization of the composition and is compatible with the skin. Suitable polymerization inhibitors are well known in the art and include 4-methoxyphenol (50 to 500 ppm based on weight of composition absent any antimicrobial agent) and sulfur dioxide (50 to 500 ppm based on weight of composition absent any antimicrobial agent). Other preferred polymerization inhibitors include glacial acetic acid, free radical inhibitors (e.g. hydroquinones) and the like which can be used alone or in combination with 4-methoxyphenol and/or $SO_2$.

The term "antimicrobial agent" refers to an agent which destroys microbes (i.e., bacteria, fungi, yeasts and viruses) thereby preventing their development and their pathogenic action. Preferably the antimicrobial agent is a complex of iodine molecules with a biocompatible polymer, more preferably the antimicrobial agent is polyvinylpyrrolidinone polymer complexed with iodine.

Compositions

The cyanoacrylate ester compositions comprising the polymerizable cyanoacrylate esters are prepared by conventional methods of mixing the appropriate components until homogenous.

The specific viscosity of these compositions depends, in part, on the intended application of the composition. For example, relatively low viscosities are often preferred where application is to be made to a large surface area. This preference results from the fact that those forms are less viscous and, accordingly, will permit more facile large surface area application of a thin layer. Contrarily, where application is to be made to a specific position on the skin (e.g., elbow surfaces), higher viscosity compositions, including those containing thixotropic materials, are preferred to prevent "running" of the material to unintended locations.

Accordingly, these compositions have a viscosity of from about 2 to 50,000 centipoise at 20° C. Preferably the less viscous compositions have a viscosity of from about 2 to 1,500 centipoise at 20° C. More preferably, the cyanoacrylate adhesive is almost entirely in monomeric form and the composition has a viscosity of from about 5 to about 500 centipoise at 20° C.

A thickening agent is optionally employed to increase the viscosity of the composition which thickening agent is any biocompatible material which increases the viscosity of the composition. Suitable thickening agents include, by way of example, polymethyl methacrylate (PMMA) or other preformed polymers soluble or dispersible in the composition, a suspending agent such as fumed silica and the like with PMMA being preferred. Fumed silica is particularly useful in producing a gel for topical application having a viscosity of from about 1500 to 50,000 centipoise at 20° C. Suitable thickening agents for the compositions described herein also include a partial polymer of the alkyl cyanoacrylate as disclosed in U.S. Pat. Nos. 3,654,239[9] and 4,038,345[10] both of which are incorporated herein by reference in their entirety.

Thickening agents are deemed to be biocompatible if they are soluble or dispersible in the composition and are compatible with the skin as measured by the lack of moderate to severe skin irritation.

In a preferred embodiment, the cyanoacrylate ester composition further comprises a therapeutically effective amount of a corticosteroid. The corticosteroid is then released from the resulting polymeric film formed in situ on the mammalian skin and serves to medicate the dermatosis and decreases discomfort such as itching, while facilitating healing of the skin. In a particularly preferred embodiment, the cyanoacrylate ester compositions preferably comprise from about 0.1 to about 25 weight percent of the corticosteroid as a solution, an emulsion or as a suspension based on the total weight of the composition.

The use of a corticosteroid in the composition permits the steroid to be released from the polymeric film thereby reducing inflammation under the film as well as to facilitate healing of the skin. Since the film is maintained over the skin for 1–4 days after formation, sustained release of steroid is achieved without the need to reapply the steroid at more frequent intervals.

In another preferred embodiment, the cyanoacrylate ester composition further comprises an antimicrobially effective amount of an antimicrobial agent which serves to inhibit microbial infection of the skin during the healing process. Preferably, the cyanoacrylate ester compositions comprise from about 1 to about 40 and more preferably 5 to 30 weight percent of the compatible antimicrobial agent either as a solution or as a suspension based on the total weight of the composition. Compatible antimicrobial agents are those which are either soluble or suspendable in the cyanoacrylate ester composition, which do not cause premature polymerization or prevent polymerization of the cyanoacrylate ester composition when applied to mammalian skin, and which are compatible with the intended use including biocompatibility with the patient's skin.

In a particularly preferred embodiment, the compatible antimicrobial agent comprises a complex of iodine molecules with a biocompatible polymer. Such complexes are well known in the art and the resulting complex typically comprises both available iodine and iodide anions. These complexes, on contact with mammalian skin, provide for a source of antimicrobial iodine. In any event, such complexes are employed only as starting materials herein and, by themselves, do not form a part of this invention. Suitable biocompatible polymers include, by way of example only, polyvinylpyrrolidinone polymer which, when complexed with iodine, is also referred to under the common name of povidone-iodine available from BASF, Mt. Olive, N.J., USA. When povidone-iodine is employed in the cyanoacrylate ester composition, it is preferably from about 5 to about 40 weight percent and more preferably from about 10 to 25 weight percent is added to the cyanoacrylate ester composition based on the total weight of the composition.

Cyanoacrylate compositions comprising, for example, povidone-iodine are described by Greff, et al., U.S. Pat. No. 5,684,042[11] which patent is incorporated herein by reference in its entirety.

Other suitable antimicrobial agents include complexes of iodine molecules with copolymers of vinylpyrrolidinone and vinyl acetate, copolymers of vinylpyrrolidinone and vinyl acetate cross-linked with polyisocyanates, copolymers of vinylpyrrolidinone and vinyl functionalities, polymers of pyrrolidone and the like. Preferably, however, the iodine containing polymer is povidone iodine which is commercially available from a number of sources.

The use of a compatible antimicrobial agent in the composition permits the agent to be released from the polymeric film thereby reducing microbial growth under the film. Again, since the film is maintained over the skin for 1–4 days after formation, there is sustained release of antimicrobial agent to retard microbial growth under the film.

The corticosteroid and antimicrobial agent can be used together or separately in the cyanoacrylate ester composition.

In addition, the cyanoacrylate adhesive compositions preferably include a biocompatible plasticizer and such plasticizers are preferably included in the composition at from about 10 to 30 weight percent and more preferably at from about 18 to 25 weight percent based on the total weight of the composition absent any antimicrobial agent.

Additionally, the cyanoacrylate ester compositions described herein preferably include a polymerization inhibitor in an effective amount to inhibit premature polymerization of the composition. In one embodiment the inhibitor is sulfur dioxide which is employed at from about 50 to 1000 ppm, preferably from 100 to 500 ppm, based on the total weight of the composition absent any antimicrobial agent. In another embodiment, the inhibitor is 4-methoxyphenol which is employed at from about 50 to 1000 ppm, preferably from 100 to 500 ppm, based on the total weight of the composition absent any antimicrobial agent. In a particularly preferred embodiment where the cyanoacrylate composition additionally comprises povidone-iodine, this inhibitor is 4-methoxyphenol which is employed at from about 50 to 500 ppm based on the total weight of the composition absent any antimicrobial agent.

The polymerizable cyanoacrylate ester compositions may additionally contain one or more optional additives such as colorants, perfumes, rubber modifiers, modifying agents, etc. In practice, each of these optional additives should be both miscible and compatible with the cyanoacrylate ester composition and the resulting polymer. Compatible additives are those that do not prevent the use of the cyanoacrylates in the manner described herein.

In general, colorants are added so that the polymer layer formed on the skin will contain a discrete and discernable color. In some cases, the colorant can be used to mask the polymer layer over the skin thereby minimizing the patient's sensitivity to the placement of such films on the skin. Perfumes are added to provide a pleasant smell to the formulation. Rubber modifiers are added to further enhance the flexibility of the resulting polymer layer. The amount of each of these optional additives employed in the composition is an amount necessary to achieve the desired effect.

Preferred cyanoacrylate ester compositions useful in the practice of this invention are also disclosed by Greff, et al., U.S. Pat. No. 5,480,935[12], which patent is incorporated herein by reference in its entirety.

In an alternative embodiment, the cyanoacrylate composition is provided in a kit of parts which comprises the polymerizable cyanoacrylate stored in a first container and the corticosteroid stored in a second container. At the appropriate point in time the contents can be mixed together to form the composition described above. Preferably, the first or second container comprises an applicator means such that upon mixing of the components the composition can be applied to mammalian skin. Alternatively, separate applicator means can be employed in the kit. In still a further preferred embodiment, the kit of parts contains PVP-iodine which is stored in a separate container and which can be combined with the other components as described above. The containers can be individual containers or a single container having a barrier separating the container into separate compartments.

Methods

The methods of this invention comprise the in situ formation of a cyanoacrylate polymer film on the skin surface undergoing active dermatosis. The film occludes the skin surface thereby reducing physical contact, irritation and thereby facilitating healing of the dermatosis. Moreover, the inclusion of a corticosteroid in the film reduces irritation to the skin.

The application protocol preferably involves skin preparation prior to in situ formation of the cyanoacrylate polymer film over the skin surfaces undergoing active dermatosis which typically comprises washing the skin, preferably with a soap solution. The skin is preferably dried and then an adherent polymeric film is formed over the skin by applying a cyanoacrylate ester composition to the skin surface. As noted above, this composition comprises polymerizable cyanoacrylate monomers and/or reactive oligomers, corticosteroids and optionally an antimicrobial agent, which, upon contact with the surface skin moisture, tissue protein, etc. polymerizes in situ to form a cyanoacrylate polymer film.

Polymerization occurs at ambient skin temperature while maintaining the skin surface under suitable conditions to allow polymerization to proceed. In general, the particular length of time required for polymerization will vary depending on factors such as the amount of composition applied, the temperature of the skin, the moisture content of the skin, the surface area of skin to which the composition was applied, and the like. However, in a preferred embodiment, polymerization is generally complete within about 10 to about 60 seconds while the skin is maintained at ambient conditions. During this period, the patient is maintained in a position which permits the cyanoacrylate ester to polymerize and form a polymeric film while minimizing any patient movement which might dislodge the cyanoacrylate ester or create undesirable bonding.

Sufficient amounts of the cyanoacrylate ester composition are employed to cover (i.e., coat) the skin area with a layer of the cyanoacrylate polymer. If necessary, excess cyanoacrylate monomer can be removed from the skin with a wipe or tissue paper before polymerization or, after polymerization, any polymer formed at unintended sites can be removed with acetone (nail polish remover).

After polymerization, the resulting polymeric film strongly adheres to the skin, is flexible and waterproof thereby forming an occlusive layer over the skin. Such strong adherence effectively eliminates the possibility that the film will separate from the patient's skin. However, notwithstanding such strong adherence, the polymeric film will only adhere to the skin for a period of about 1–4 days after which time it sloughs off. This occurs because the cyanoacrylate polymer adheres only to the uppermost portion of the epidermal layer which is continuously in the process of being sloughed off and replaced by the underlying cells. Accordingly, additional cyanoacrylate ester composition can be applied to the skin if it is desired to maintain the polymeric film over the skin and continue treatment with the corticosteroid and, optionally, the antimicrobial agent.

The polymeric film should be maintained in an unbroken manner over the skin surface undergoing active dermatosis. This can be assured by careful application of the cyanoacrylate composition onto the skin. Additionally, the use of a plasticizer in the composition will facilitate the maintenance of the polymeric film in an unbroken manner and will inhibit cracking of the film.

In one preferred embodiment, after the initial polymeric film is formed, a second, preferably thinner, coating of cyanoacrylate ester composition is applied thereto. Additional amounts of cyanoacrylate ester composition can be applied as needed to maintain an unbroken coating over the surface skin areas.

Application is conducted under conditions wherein the polymeric film has a thickness of no more than about 1 millimeter and, more preferably, the polymer film has a thickness of from about 2 to about 500 microns and still more preferably from about 20 to about 100 microns. If thinner polymeric films are desired, then the polymeric film should have a thickness of from about 2 to about 50 microns and preferably from 10 to 40 microns. One drop of the cyanoacrylate ester composition can cover from about 5 $cm^2$ to about 25 $cm^2$ area. The amount of cyanoacrylate ester composition applied to a unit area of skin to obtain such thicknesses is well within the skill of the art.

After polymerization, the cyanoacrylate film has biostatic properties[3]. In one particularly preferred embodiment, the cyanoacrylate ester composition further comprises a compatible antimicrobial agent to provide antimicrobial properties to the composition.

The size and thickness of the polymeric film formed over the skin surface area can be readily controlled by the amount and viscosity of cyanoacrylate ester composition packaged in a single dose product or by use of a multiple use dispenser which governs the amount of material applied onto a unit area of surface skin. In this regard, the dispenser described by Otake, U.S. Pat. No. 4,958,748, which is incorporated by reference in its entirety, is one example of a dispenser which dispenses the cyanoacrylate adhesive composition in a controlled dropwise manner. Other methods for the controlled dispersement of the cyanoacrylate adhesive include, by way of example, a spray applicator, brush, wipe, swab or solid paddle applicator, applicators for repeated and intermittent use of the cyanoacrylate ester composition and the like.

In applicators, the cyanoacrylate ester composition is stored at ambient conditions. The cyanoacrylate ester composition may be provided as a sterile solution or may be sterilized as needed.

Because the cyanoacrylate polymer film is waterproof, the patient is not prevented from bathing or being bathed and other activities involving exposure to water during the period the polymer film protects the skin surface undergoing active dermatosis.

The following examples illustrate certain embodiments of the invention but are not meant to limit the scope of the claims in any way.

EXAMPLES

Example 1

This example examines the compatibility of a corticosteroid agent in a cyanoacrylate ester composition. In particular, the composition employed monomeric n-butyl cyanoacrylate containing 100 ppm sulfur dioxide and 20 weight percent of dioctyl phthalate absent the corticosteroid. Five (5) weight percent of hydrocortisone (Aldrich), based on the total weight of the composition, was added thereto and the properties of the resulting composition evaluated.

The evaluation included assessing whether the corticosteroid was soluble or suspendable in the composition; whether the resulting composition cured upon contact with skin; whether curing provided for a polymeric film in situ on the skin; whether the polymeric film was flexible and durable. Solubility and suspendability were determined by conventional standards (visual observation). The ability of the resulting composition to cure in situ upon application to skin was measured by applying the cyanoacrylate ester composition onto the upper arm of a male human subject and determining whether polymerization proceeded (up to 5 minutes) and, if so, the time required for polymerization. Film forming capabilities on the skin were assessed by visual evaluation. Durability was assessed by determining whether the film was retained on the skin surface for at least 24 hours and flexibility was measured by the ability of the film to be retained on the skin without cracking or peeling for at least 24 hours. The results of this evaluation are summarized in Table I below:

TABLE I

| Corticosteroid | Conc. | Soluble | Curable | Film Formed | Flex. | Dur. |
|---|---|---|---|---|---|---|
| Hydro-cortisone | 5% | Yes | Yes | Yes | Yes | Yes |

The composition described above did not result in premature polymerization for period of at least two months at room temperature.

The results of this example illustrate that hydrocortisone is compatible with the cyanoacrylate ester.

Example 2

This example illustrates how a cyanoacrylate ester composition comprising hydrocortisone could be used to treat a skin lesion arising from psoriasis. In this example, the cyanoacrylate ester composition is the same as that described in Example 1 above.

Initially, a psoriatic lesion measuring 6 square centimeters in area located on the upper arm of a male human patient is washed with soap and then dried. One drop of the cyanoacrylate ester composition of Example 1 above is placed on and spread with the fingertip over the lesion. About 30 seconds is allowed for polymerization of the composition whereupon a solid, coherent polymeric film forms over the lesion which film occludes the lesion. Moreover, there is a sustained release of hydrocortisone from the film which medicates the lesion. After formation of the polymeric film, the patient may wash or cover the upper arm, e.g., with clothing, without irritation or the film rubbing off.

Example 3

A cyanoacrylate ester composition is prepared as per Example 1 above but further comprises 10 weight percent of PVP-$I_2$ as an antimicrobial agent. A psoriatic lesion measuring 5 square centimeters in area located on the back of a female human patient is washed with soap and then dried. One drop of this cyanoacrylate ester composition is placed on and spread with a fingertip over the lesion. About 60 seconds is allowed for polymerization of the composition whereupon a solid, coherent polymeric film forms over the lesion which film occludes the lesion. Moreover, there is a sustained release of both hydrocortisone and iodine from the film which medicates the lesion. After formation of the polymeric film, the patient may wash or cover the back, e.g., with clothing, without irritation or the film rubbing off.

From the foregoing description, various modifications and changes in the composition and method will occur to those skilled in the art. All such modifications coming within the scope of the appended claims are intended to be included therein.

What is claimed is:

1. A method for forming an occlusive layer over the surface of dermatosis on mammalian skin surfaces which method comprises:

(a) applying directly to the topical surface of the dermatosis a polymerizable cyanoacrylate ester composition which composition comprises a polymerizable cyanoacrylate ester and from about 0.1 to about 25 weight percent of a corticosteroid based on the entire weight of the composition; and (b) polymerizing the cyanoacrylate ester composition in situ on said surface so as to form a coherent polymeric film over the dermatosis.

2. The method according to claim 1 wherein the polymerizable cyanoacrylate ester is a polymerizable monomer or reactive oligomer of a cyanoacrylate ester which, in monomeric form, is represented by formula I:

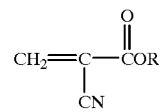

I wherein R is selected from the group consisting of:
alkyl of 1 to 10 carbon atoms,
alkenyl of 2 to 10 carbon atoms,
cycloalkyl groups of from 5 to 8 carbon atoms,
phenyl,
2-ethoxyethyl,
3-methoxybutyl,
and a substituent of the formula:

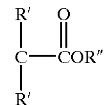

wherein each R' is independently selected from the group consisting of:
hydrogen and methyl, and
R" is selected from the group consisting of:
alkyl of from 1 to 6 carbon atoms,
alkenyl of from 2 to 6 carbon atoms,
alkynyl of from 2 to 6 carbon atoms,
cycloalkyl of from 3 to 8 carbon atoms,
aralkyl selected from the group consisting of benzyl, methylbenzyl and phenylethyl,
phenyl, and
phenyl substituted with 1 to 3 substituents selected from the group consisting of hydroxy, chloro, bromo, nitro, alkyl of 1 to 4 carbon atoms, and alkoxy of from 1 to 4 carbon atoms.

3. The method according to claim 2 wherein R is alkyl of from 4 to 10 carbon atoms.

4. The method according to claim 3 wherein R is alkyl of from 4 to 8 carbon atoms.

5. The method according to claim 4 wherein R is selected from the group consisting of butyl, pentyl, octyl or decyl.

6. The method according to claim 5 wherein R is n-butyl.

7. The method according to claim 1 wherein said corticosteroid is selected from the group consisting of cortisone, desoximetasone, hydrocortisone, betamethasone and fluorinated derivatives.

8. The method according to claim 1 wherein said cyanoacrylate ester composition further comprises an antimicrobial agent.

9. The method according to claim 8 wherein the antimicrobial agent is PVP-$I_2$.

10. The method according to claim 1, wherein said cyanoacrylate oster composition further comprises an antimicrobial agent.

11. The method according to claim 10 wherein the antimicrobial agent is PVP-$I_2$.

12. The method according to claim 1 wherein said cyanoacrylate ester composition further comprises a biocompatible plasticizer.

13. The method according to claim 12 wherein said biocompatible plasticizer is dioctyl phthalate or $C_2$–$C_4$ acyl tri-n-alkyl ($C_1$–$C_6$) citrates.

14. The method according to claim 1 wherein said cyanoacrylate ester composition further comprises a polymerization inhibitor.

15. The method according to claim 11 wherein said polymerization inhibitor is $SO_2$.

16. The method according to claim 1 wherein said dermatosis on the mammalian skin surface is associated with psoriasis, dermatitis, eczema, and topical skin irritation due to alkyl catechols.

17. A cyanoacrylate ester composition which comprises:

(a) a polymerizable cyanoacrylate ester; and (b) from about 0.1 to about 25 weight percent of a corticosteroid based on the entire weight of the composition.

18. The cyanoacrylate ester composition according to claim 17 wherein the polymerizable cyanoacrylate ester is a polymerizable monomer or reactive oligomer of a cyanoacrylate ester which, in monomeric form, is represented by formula I:

I

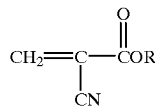

wherein R is selected from the group consisting of:
- alkyl of 1 to 10 carbon atoms,
- alkenyl of 2 to 10 carbon atoms,
- cycloalkyl groups of from 5 to 8 carbon atoms,
- phenyl,
- 2-ethoxyethyl,
- 3-methoxybutyl,
- and a substituent of the formula:

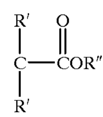

wherein each R' is independently selected from the group consisting of:
- hydrogen and methyl, and R" is selected from the group consisting of:
- alkyl of from 1 to 6 carbon atoms,
- alkenyl of from 2 to 6 carbon atoms,
- alkynyl of from 2 to 6 carbon atoms,
- cycloalkyl of from 3 to 8 carbon atoms,
- aralkyl selected from the group consisting of benzyl, methylbenzyl and phenylethyl,
- phenyl, and
- phenyl substituted with 1 to 3 substituents selected from the group consisting of hydroxy, chloro, bromo, nitro, alkyl of 1 to 4 carbon atoms, and alkoxy of from 1 to 4 carbon atoms.

19. The cyanoacrylate ester composition according to claim 18 wherein R is alkyl of from 4 to 10 carbon atoms.

20. The cyanoacrylate ester composition according to claim 19 wherein R is alkyl of from 4 to 8 carbon atoms.

21. The cyanoacrylate ester composition according to claim 20 wherein R is selected from the group consisting of butyl, pentyl, octyl or decyl.

22. The cyanoacrylate ester composition according to claim 21 wherein R is n-butyl.

23. The cyanoacrylate ester composition according to claim 17 wherein said corticosteroid is selected from the group consisting of cortisone, desoximetasone, hydrocortisone, betamethasone and fluorinated derivatives.

24. The cyanoacrylate ester composition according to claim 17 wherein said cyanoacrylate ester composition further comprises an antimicrobial agent.

25. The cyanoacrylate ester composition according to claim 24 wherein the antimicrobial agent is PVP-$I_2$.

26. The cyanoacrylate ester composition according to claim 17 wherein said cyanoacrylate ester composition further comprises an antimicrobial agent.

27. The cyanoacrylate ester composition according to claim 26 wherein the antimicrobial agent is PVP-$I_2$.

28. The cyanoacrylate ester composition according to claim 17 wherein said cyanoacrylate ester composition further comprises a biocompatible plasticizer.

29. The cyanoacrylate ester composition according to claim 28 wherein said biocompatible plasticizer is dioctyl phthalate or $C_2$–$C_4$ acyl tri-n-alkyl ($C_1$–$C_6$) citrates.

30. The cyanoacrylate ester composition according to claim 17 wherein said cyanoacrylate ester composition further comprises a polymerization inhibitor.

31. The cyanoacrylate ester composition according to claim 30 wherein said polymerization inhibitor is $SO_2$.

* * * * *